(12) United States Patent
McConnaughey et al.

(10) Patent No.: US 12,268,799 B2
(45) Date of Patent: Apr. 8, 2025

(54) DEVICE CONTAINING AIR DETECTION, FILTERING, DISINFECTING AND CONDITIONING ELEMENTS WITH DISPLAY

(71) Applicant: IATRIXAIR, INC, Temecula, CA (US)

(72) Inventors: Joseph Marc McConnaughey, Temecula, CA (US); Zuoyu Shi, San Ramon, CA (US); Chang Chia Jung, New Taipei (TW); Stephens A. Hutchcraft, III, Alamo, CA (US)

(73) Assignee: IATRIXAIR, INC., Temecula, CA (US)

( * ) Notice: Subject to any disclaimer, the term of this patent is extended or adjusted under 35 U.S.C. 154(b) by 731 days.

(21) Appl. No.: 17/403,303

(22) Filed: Aug. 16, 2021

(65) Prior Publication Data
US 2022/0047767 A1 Feb. 17, 2022

Related U.S. Application Data (60) Provisional application No. 63/065,786, filed on Aug. 14, 2020.

(51) Int. Cl.
*A61L 9/20* (2006.01)
*A61L 9/22* (2006.01)
(Continued)

(52) U.S. Cl.
CPC ............ *A61L 9/20* (2013.01); *A61L 9/22* (2013.01); *B01D 46/0028* (2013.01); *B01D 46/0038* (2013.01); *B01D 46/429* (2013.01); *B01D 46/44* (2013.01); *B01D 46/62* (2022.01); *A61L 2209/111* (2013.01); *A61L 2209/12* (2013.01); *A61L 2209/14* (2013.01); *B01D 2273/30* (2013.01); *B01D 2279/65* (2013.01)

(58) Field of Classification Search
CPC ........ A61L 9/20; A61L 9/22; A61L 2209/111; A61L 2209/12; A61L 2209/14; A61L 2209/15; B01D 46/62; B01D 46/546; B01D 46/429; B01D 46/0028; B01D 46/0038; B01D 46/44; B01D 2239/025; B01D 2239/0258; B01D 2259/804; B01D 2267/40; B01D 2267/70; B01D 2279/65; B01D 2273/30
See application file for complete search history.

(56) References Cited

U.S. PATENT DOCUMENTS
2008/0019861 A1  1/2008  Silderhuis

FOREIGN PATENT DOCUMENTS
| WO | 2016116656 A1 | 7/2016 |
| WO | 2019084592 A1 | 5/2019 |
| WO | 2019158545 A1 | 8/2019 |

OTHER PUBLICATIONS
International Search Report and Written Opinion dated Nov. 30, 2021 for PCT/US21/46050.

*Primary Examiner* — Lessanework Seifu
(74) *Attorney, Agent, or Firm* — Reed Smith LLP; Nina Habib Borders (57) ABSTRACT

Disclosed is a device for purifying or disinfecting contaminated air in an environment comprising a filter stack comprising a HEPA filter coated with a nanopolymer configured to puncture virus particles, a light chamber comprising UVC light source and an ion generator, where in the device is configured to take in contaminated air at the top of the device and expel purified air downward and away from each end of the device.

16 Claims, 7 Drawing Sheets

(51) Int. Cl.
*B01D 46/00* (2022.01)
*B01D 46/42* (2006.01)
*B01D 46/44* (2006.01)
*B01D 46/62* (2022.01)

DEVICE CONTAINING AIR DETECTION, FILTERING, DISINFECTING AND CONDITIONING ELEMENTS WITH DISPLAY

CROSS-REFERENCE TO RELATED APPLICATION

This application claims the benefit of U.S. Provisional Patent Application Ser. No. 63/065,786 filed on August 14, 2020 under 35 U.S.C. § 119, the entire disclosure of which is incorporated herein by reference.

BACKGROUND

UVC and UVA light is proven to disinfect air and surfaces. Medical grade HEPA filters are proven to filter viruses, bacteria and mold spores.

Conventional HVAC systems are designed to recycle air. Virus particles responsible for CV-19 are known to stay longer in the air like an aerosol. In commercial and home HVAC systems air flow is uneven and may be spreading the virus. It is not easy to re-design the HVAC systems to bring in fresh air and if so, more pollutants can enter the commercial or home spaces. Localized, in space air purification and disinfection devices are useful to augment air purity in enclosed spaces.

With CV-19, it is now showing that air should be pushed downward, pushing pollutants away-not up into the air since the CV-19 virus is very airborne. Conventional air purifiers are floor standing devices mostly filtering air by taking air in at the floor level where most pollutants are, then releasing them upward with some now providing some type of virus, bacteria killing function.

SUMMARY OF THE DISCLOSED SUBJECT MATTER

This disclosure provides a device that allows for a top intake vent that brings air first to a HEPA Medical Grade Filter coated with a virus inactivating nanopolymer for filtering, then into a UVC lamp or LED or excimer based light chamber or engine which rapidly disinfects the air with exhaust exits on the right and left ends that shoot the air downward toward the floor. In some embodiments the HEPA Medical Grade Filter may be a HEPA H13 Medical Grade Filter.

The device comprises:
an air intake configured to take in contaminated air from an environment in fluid communication with a filter stack comprising a prefilter, carbon filter and separate HEPA filter, wherein the HEPA filter is coated with a nanopolymer configured to puncture or inactivate virus particles, wherein the filter stack is configured to provide filtered air;
wherein the filter stack is in fluid communication with a light chamber enclosing a high intensity UVC light source including for example a UVC lamp and/or UVC LED; and wherein the light chamber further comprises an ion generator wherein the filtered air from the filter stack is treated with the UVC light source killing up to approximately 99.7% of viruses, bacteria and mold spores and the ion generator of negative and positive ions that are released to attach to particulates in the occupied space, providing additional purification of the air;
wherein the light chamber is in fluid communication with a fan on each of opposed ends of the device, wherein the fans are configured to move air from the air intake through the filter stack and the light chamber and expel purified air downward from the device and back into the environment;
one or more sensors that, in some embodiments, may be mounted inside the device or in a separate sensor gateway box that may be placed in other areas of the space to sense the condition of the air including, for example and without limitation, VOC, formaldehyde, particle, smoke, radon, temperature, humidity, air pressure, noise/sound for presence, $CO_2$, and/or CO as it passes through the device or through the sensor gateway box; and
a controller in operational communication with the one or more sensors that, in some embodiments, may turn on every 2-5 seconds, the UVC light source, the ion generator and the fans to monitor and control operation of the device, wherein the controller analyzes the sensor data locally and is also in wireless communication to a cloud based service that then analyzes and prepares air quality information and alerts that are sent to a remote user interface such as a mobile application or to a bright, large display mounted to the front of the device.

The device has internal sensors to detect, for example and without limitation, temperature, humidity, UVC Light flux, VOC gases, particulate size down to 1 micron, and an internal bi-polar ionizer that emits positive and negative ions that are then passed externally. The front door of the industrial design has thermal and motion sensors and can open providing UVC light to disinfect the air and surfaces. On the top and bottom of the device are UVA, Circadian light and other LED light therapy light guides. The device is Internet-of-Things (IOT) connected via LTE/5G, WIFI and Bluetooth Mesh and sends data gathered by the sensors to the cloud and to a mobile application, or to an internal or external display to inform the user of how the device is detecting and preventing viruses, bacteria, mold spores and other dangerous particulates.

An embodiment of the device comprises a door on the light chamber equipped with a servo motor and thermal-motion sensor configured to detect room occupancy by a person, child or pet, wherein the servo motor opens the door when the room is unoccupied to allow the UVC light to shine into the room and closes the door when the room is occupied.

The invention also provides a method for purifying contaminated air in an environment, the method comprising:
taking contaminated air into the top of the device described above,
filtering the contaminated air through a filter stack comprising a prefilter, carbon filter and HEPA filter, wherein the HEPA filter is coated with a nanopolymer configured to puncture virus particles to provide filtered air;
passing the filtered air into a light chamber enclosing a high intensity UVC light source or multiple sources and an ion generator;
treating the filtered air with the UVC light source and the ion generator to provide disinfected air;
passing the disinfected air through another carbon filter for further purification and through the fans on each of opposed ends or at the bottom of the device; and
expelling the purified air downward from the device and back into the environment.

DETAILED DESCRIPTION OF THE DISCLOSED SUBJECT MATTER

The disclosed device is designed to take air from the top of the room, purify it and push it downwards and do this as many times an hour as possible.

The design is based on the physics of filtering, puncturing, light wavelengths, ions and air flow and comprises the following elements.

A HEPA H13 filter that traps up to 99.7% down to 0.1 micron

A nanopolymer that inactivates viruses and bacteria to 99% by physically puncturing An internal UVC lamp light kills 99.9% so of 100 people perhaps only 0.1% maybe affected The single intake and two fans left and right exchange the air very fast. The device has variable speed levels of increasing CFM based on the two fans designed in.

An ion generator provides for additional layer of defense with negative and positive ions that are released out to occupied or nonoccupied space by the right and left fans and attach to particulates rendering these particulates inactive. The negative ions may be passed to the right fan and positive ions to the left fan, thereby maximizing the ions released to the occupied or unoccupied space which provides for higher attachment and inactivation of particulates in that space.

405 nm light-emitting diodes (LEDs) can clean the air and surfaces up to 90% of bacteria depending on distance.

The device works by having an internal light engine structure with two fans, one located left and one right that brings in the air from the top vent intake, through the thick HEPA H13 filter stack coated with a nano polymer that can inactivate viruses and bacteria into the light chamber where the high powered UVC light is mounted.

The device provides air changes beyond current industry air change standards, in which the faster air changes improves cleaning the air and provides greater safety.

First pass kill or inactivation rates of 99.9% using light sources of intensified UVC light and engineered to IEC13485 standards for Class II medical devices and submitted to the FDA/EPA among other industry certifications. The multiple layers of defense or cumulative approach means significantly less virus aerosols in enclosed spaces.

It also provides cloud connectivity via LTE/5G, WIFI or Bluetooth to provide timely information and feedback about air quality from particle and other sensors.

Our device uses non-ozone light sources and does not use chemical reactions such as photochemical reactions (PECO) to inactivate pollutants. Also, there is no one way to provide safety and cumulative approaches is important. which is why we have multiple layers of proven technologies from HEPA to Nanocoating to UVC light with downward air flow.

Figure 1:
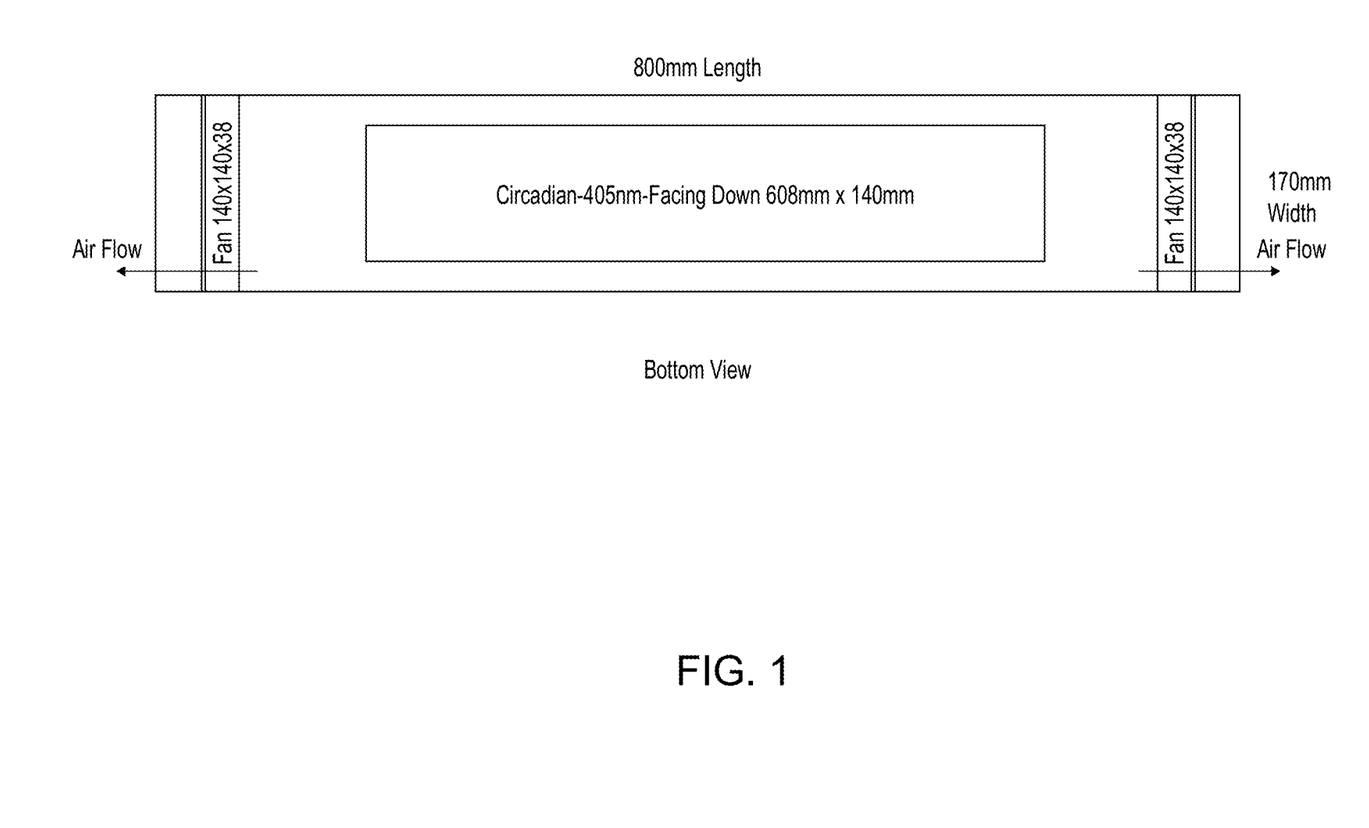
FIG. 1 shows a schematic view of the bottom of a device according to an embodiment of the disclosed subject matter.
Figure 2:
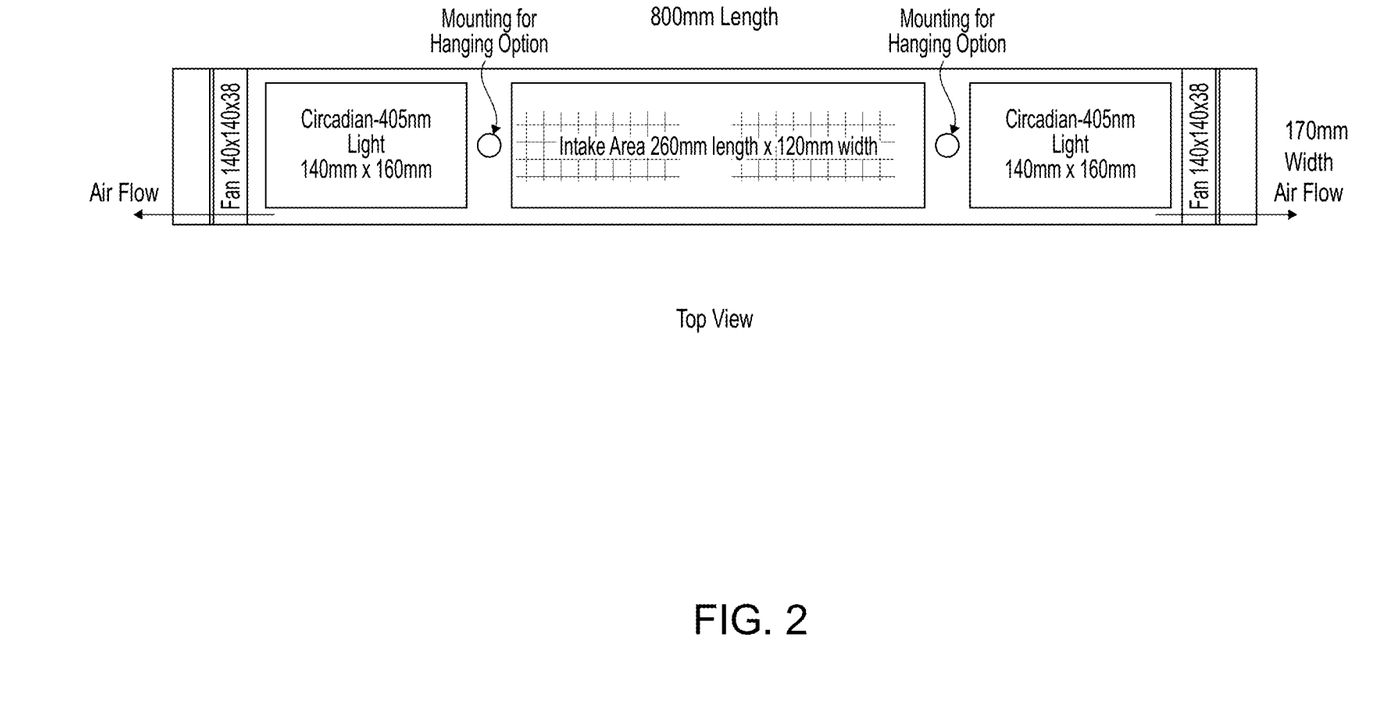
FIG. 2 shows a schematic view of the top of a device according to an embodiment of the disclosed subject matter.
Figure 3:
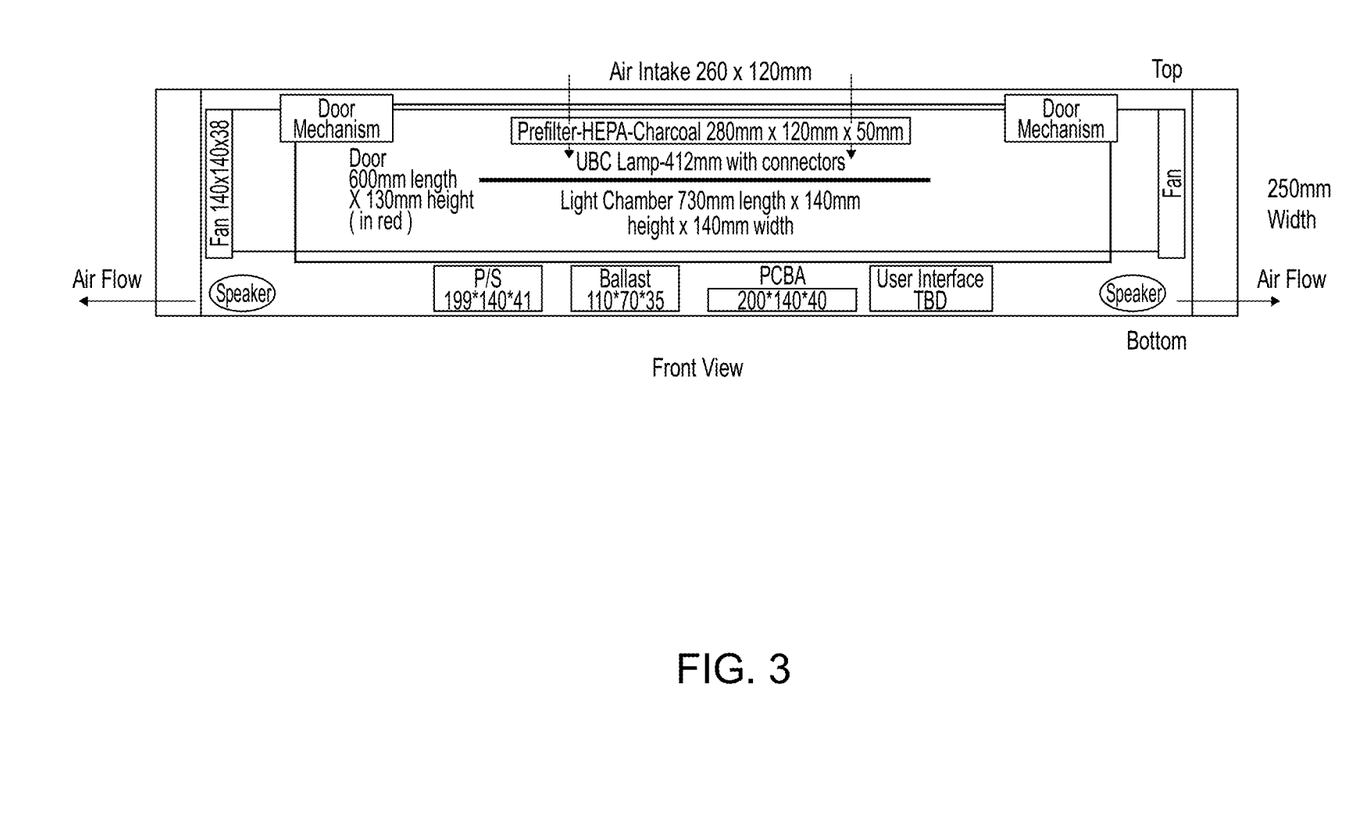
FIG. 3 shows a schematic view of the front of a device according to an embodiment of the disclosed subject matter.

This device provides multiple layers of defense to improve our safety and wellness at work, at home and in public places. As shown in FIGS. 1, 2, and 3, the industrial design of the device is like a sound bar in form factor, which provides the functionality of the product to take air in at the top and out the sides and downward such that it can be mounted up on a wall.

FIG. 1 shows a bottom view of the device, showing that air exiting the device is directed to right and left and directed downward by the design of the vents.

As shown in FIG. 2, the device takes in air from the top rather than the bottom like traditional air purifiers into a medical grade HEPA H13 filter mounted below the air intake with a pre-filter to remove large particles and carbon filter to reduce odors. Additionally, the HEPA filter is coated with a nano polymer that inactivates bacteria and viruses passively by punctuating the wall of the virus or bacteria. The nanopolymer may inactivate up to 99% of corona like viruses.

The air is then passed through the filters near the air intake at the top of the device to a large light chamber with a UVC high intensity lamp mounted in the middle that destroys viruses, bacteria and mold spores both in the air and on the filter. FIG. 3 shows a front view of the device showing the light chamber with the UVC lamp behind a door. The light chamber walls have reflective materials and prismatic features that intensify the light killing and inactivating dangerous viruses, bacteria, mold spores and other particulates.

Also shown are a power supply (PS), Ballast, which is a special power supply for the lamp, A printed circuit board assembly (PCBA) on which controllers, processors, communication units, etc. needed to operate the device are mounted. A user interface panel on the device provides user control of the device and status and air quality information to the user. Additionally, there may be other user interface portals including a remote control device for local user control, a mobile application and desktop dashboards in wireless communication with the device. Internet-of-Things (IOT) connectivity, for example with WIFI or Bluetooth, allows a user to monitor device performance.

Optional speakers may be mounted in the device to provide audio functionality to the user such as noise generator, music or information.

The components of the device are mounted on a metal chassis. On the back of the chassis are brackets for mounting the device on a wall, ceiling or stand (not shown).

A bi-polar ionizer is mounted in the light chamber emitting positive and negative ions to further reduce air particulates in the targeted space. Fans mounted internally at the ends of the chamber then cause the purified, disinfected and ionized air to exit either right or left and downward as the venting is angled at 45 degrees or more.

Volatile organic compound (VOC) and particle sensors are mounted in the light chamber reporting data collected to the IOT electronics and into the cloud for processing and send to a mobile application to inform the user of the device status. Additional sensors may be mounted elsewhere. For example, sensors in the filter components may provide information about filter efficiency and lifetime, etc. Airflow sensors may be useful for monitoring the volume of air such a cubic feet per minute (CFM) passing through the device.

Figure 4:
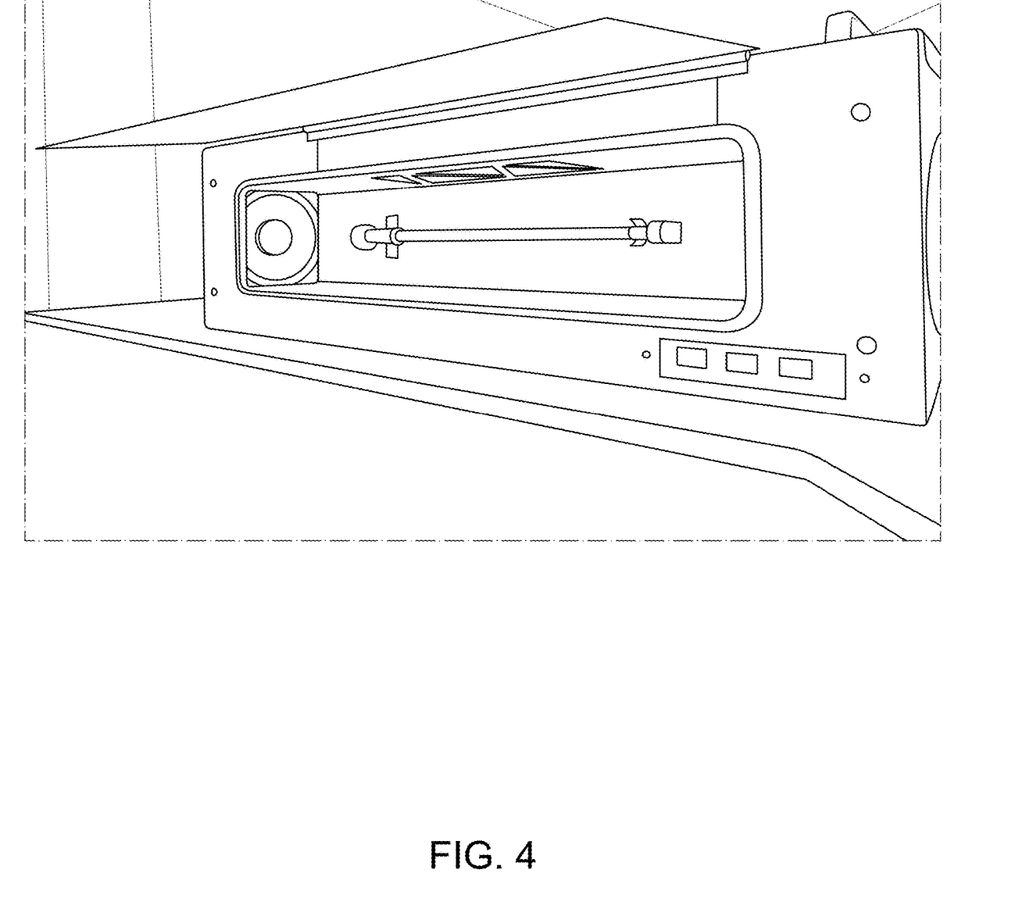
FIG. 4 shows a photograph of a device with an open door on the light chamber to show the UVC light source, according to an embodiment of the disclosed subject matter.

As shown in FIG. 4, the front of the device has a door to allow access to the interior of the device, for example to change filters, replace the UVC light, etc. In some embodiments, the door is equipped with a servo motor and thermal-motion sensor that detects room occupancy by a person, child or pet. In certain applications such as an elevator or public restroom, the front door can open up disinfecting the air and surfaces of the elevator or restroom. The thermal and motion sensor provides for auto shutoff if a person enters the space. When the room is unoccupied, the door may open up to disinfect the room's air and surfaces up to 12 feet with UVC light, providing another layer of defense. The device may also be programmed to open the door for UVC treatment when no one is in the building, such as during closed hours of a store, restaurant or office.

Additionally, as shown in FIG. 1 and FIG. 2, there are optional embedded lightguides mounted with LED's that provide 405 nm UVA light that disinfects up to 90% of the bacteria in the air and on surfaces and/or Circadian and Light Therapy LED's that can provide additional wellness functions, including red light therapy, such as at 620 to 680 nm or IR wavelengths from 720 to over 1000 nm. Sensors can indicate the use and condition of each of these elements.

Figure 5:
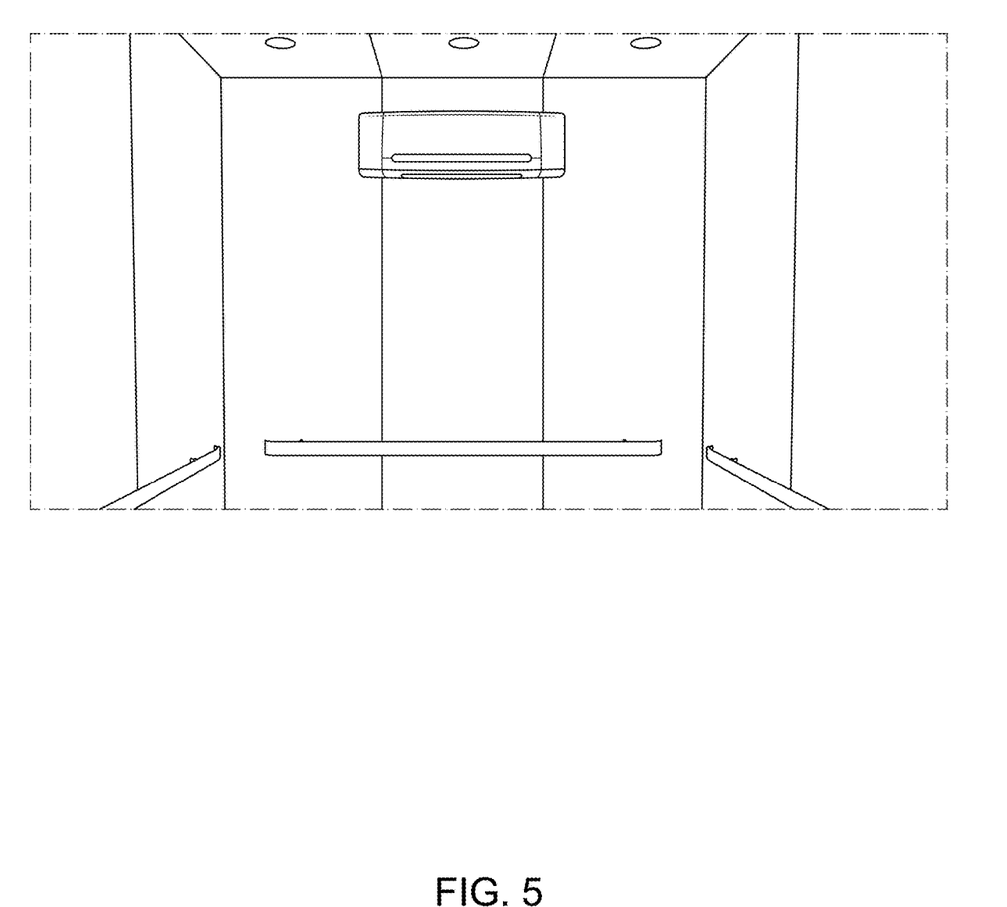
FIG. 5 shows a depiction of a device mounted on a wall, according to an embodiment of the disclosed subject matter.

The form factor allows for mounting on the wall vertically or horizontally, hung from the ceiling, placed on a stand with or without wheels. An advantage is placing the device up higher in the space to collect, filter, disinfect in many ways and push this air downward-not upward, which is the opposite of air purifiers today which are mostly tower designs to sit on the floor and push air upward. FIG. 5 shows a depiction of an exemplary device mounted on a wall. The device can be scaled down to a tabletop or desktop version all the way to large venues such as auditoriums.

Figure 6A:
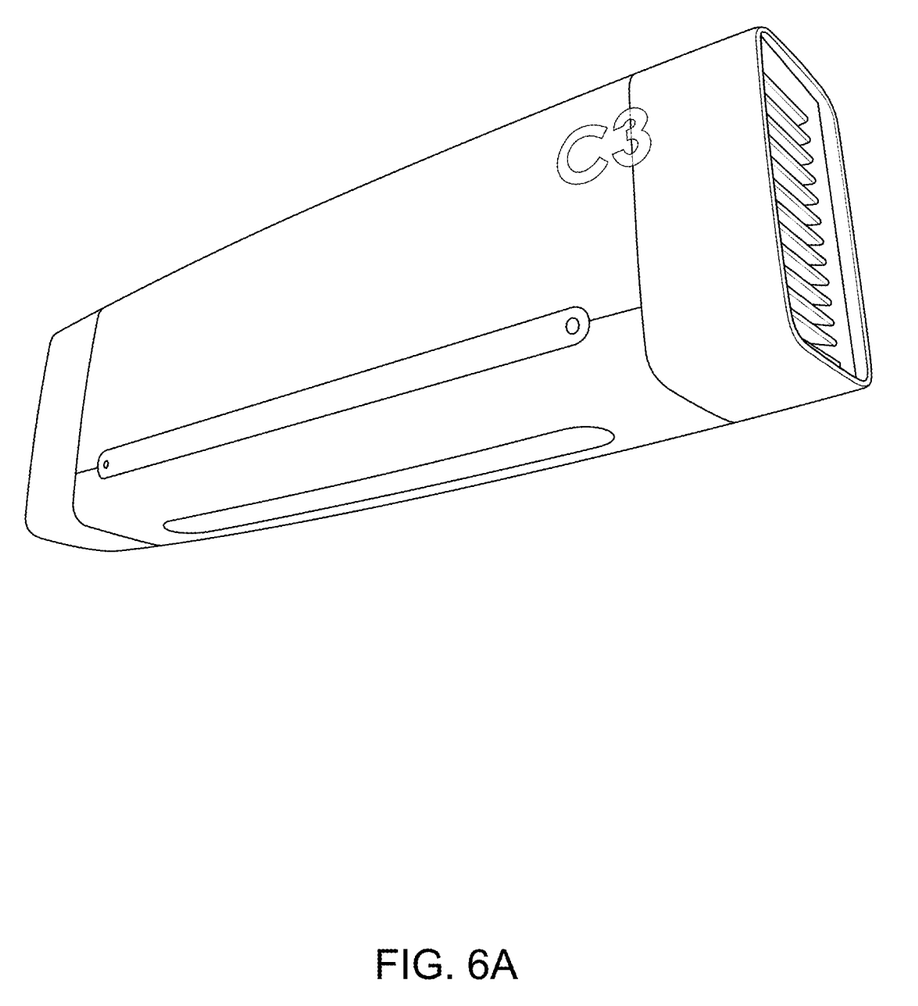
FIGS. 6A and 6B show depictions of exemplary devices in perspective view, according to an embodiment of the disclosed subject matter.
Figure 6B:
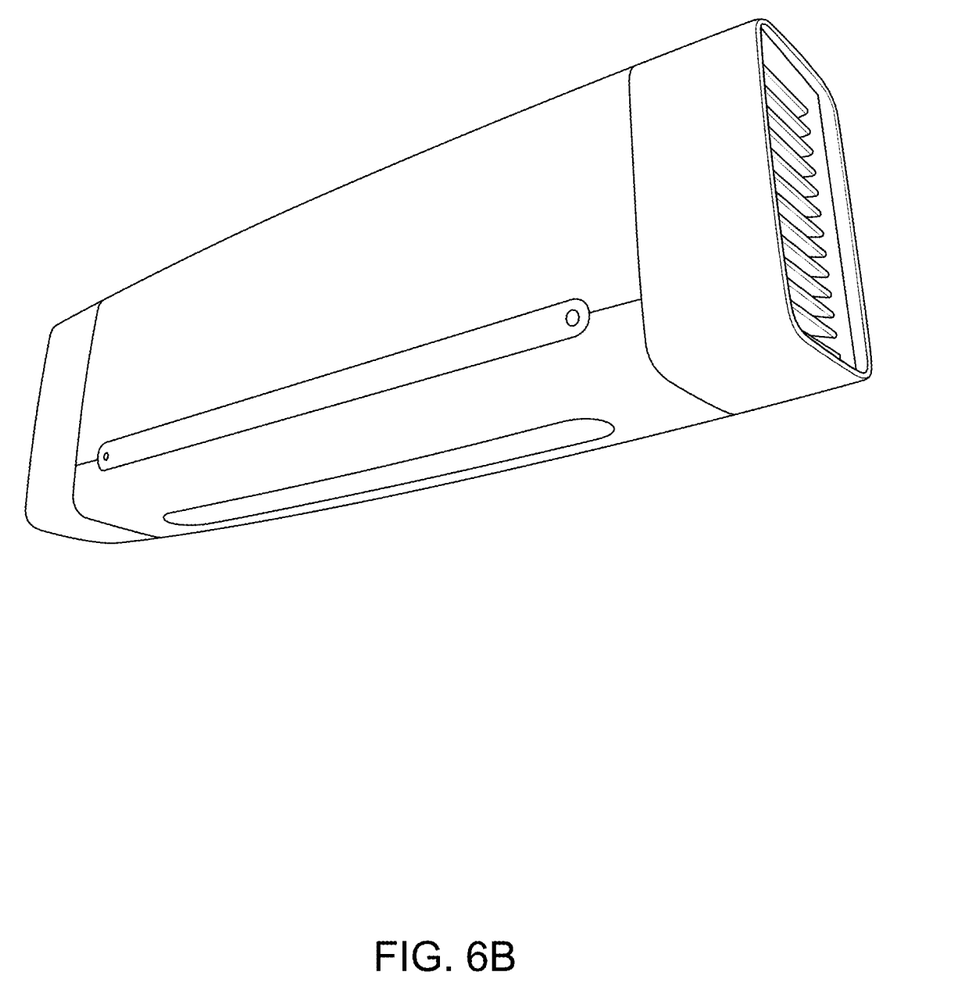

FIGS. 6A and 6B show depictions of exemplary devices in perspective view. The design is scalable from small units that can fit on a desk that provides effective layers of defense in less than 100 cubic feet to very large ones providing 10,000 or more cubic feet layers of defense.

A consumer can buy and place the device on a wall to provide layers of defense in a child's bedroom, master bedroom or family room. A hair salon, dental office, medical office, or restaurant, etc. can mount several on the walls to provide higher levels of defense to their customers. A business can mount the devices in conference rooms, offices, hallways, etc. to provide an extra level of defense against viruses, bacteria, mold spores and other air pollutants. Other places where the device can be used include hotel rooms, cruise ship rooms, dormitory rooms, classrooms, elevators, offices, subway cars, buses, RV's and any well-defined space.

The device is an advanced wellness product that improves air quality, protects against dangerous air pollutants and provides for light that can improve our wellness.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments and/or implementations may be understood and effected by those skilled in the art of practicing the claimed disclosure, from a study of the drawings, the disclosure and the appended claims.

The invention claimed is:

1. A device comprising
   an air intake configured to take in contaminated air from an environment in fluid communication with a filter stack comprising a prefilter, HEPA filter and carbon filter, wherein the HEPA filter is coated with a nanopolymer configured to puncture virus particles, wherein the filter stack is configured to provide filtered air;
   wherein the filter stack is in fluid communication with a light chamber that intensifies and encloses a high intensity UVC light source; and wherein the light chamber further comprises an ion generator wherein the filtered air from the filter stack is treated with the UVC light source and the ion generator to provide purified air;
   wherein the light chamber is in fluid communication with a first fan disposed on a first end of the device and a second fan on a second end of the device opposed to the first end, wherein the first fan and the second fan are configured to move air from the air intake through the filter stack and the light chamber and expel purified air downward from the device and back into the environment;
   wherein the ion generator generates negative and positive ions in which the negative ions are passed to the first fan and positive ions are passed to the second fan maximizing the ions released to the occupied or unoccupied space;
   one or more sensors to sense the condition of the air as it passes through the device; and
   a controller in operational communication with the one or more sensors, the UVC light source, the ion generator and the fans to monitor and control operation of the device, wherein the controller is also in wireless communication with a remote user interface.

2. The device according to claim 1 comprising a door on the light chamber equipped with a servo motor and thermal-motion sensor configured to detect room occupancy by a person, child or pet, wherein the servo motor opens the door when the room is unoccupied to allow the UVC light to shine into the room and closes the door when the room is occupied.

3. The device of claim 1 further comprising LED lights on the top and bottom of the device that can depending on the wavelength of light inactivate bacteria up to 90% or provide for light therapy.

4. The device of claim 1 wherein the device may be placed on a floor, or mounted on a wall, ceiling, or on a stand, while sending air downward.

5. The device of claim 3 wherein the LED lights are configured to emit far red light at 620 to 680 nm.

6. The device of claim 3 wherein the LED lights are configured to emit infrared light at over 700 nm to 1100 nm.

7. The device of claim 3 wherein the LED lights are configured to emit circadian light.

8. The device of claim 3 wherein the LED lights are configured to emit combinations of light selected from the group consisting of far red light at 620 to 680 nm, infrared light at over 700 nm to 1100 nm and circadian light.

9. A method for purifying contaminated air in an environment, the method comprising
   taking contaminated air into the top of the device of claim 1;
   filtering the contaminated air through a filter stack comprising a prefilter, HEPA filter and carbon filter, wherein the HEPA filter is coated with a nanopolymer configured to puncture virus particles to provide filtered air;
   passing the filtered air into a light chamber enclosing a high intensity UVC light source and an ion generator that generates negative and positive ions in which the negative ions are passed to the first fan and positive ions are passed to the second fan maximizing the ions released to the occupied or unoccupied space;
   treating the filtered air with the UVC light source and the ion generator to provide disinfected air;

passing the disinfected air through the first fan and the second fan; and expelling the disinfected air downward from the device and back into the environment.

10. The method of claim 9 wherein the device further comprises a door on the light chamber equipped with a servo motor and a thermal-motion sensor configured to detect room occupancy by a person, child or pet.

11. The method of claim 10 further comprising the servo motor opening the door to allow UVC light to shine into the room when the thermal-motion sensor detects that the room is unoccupied; or the servo motor closing the door when the thermal-motion sensor detects that the room is occupied.

12. The method of claim 9 wherein the device further comprises LED lights on the top and bottom of the device that can depending on the wavelength of light inactivate bacteria up to 90% or provide for light therapy.

13. The method of claim 12 comprising emittting far red light at 620 to 680 nm.

14. The method of claim 12 comprising emittting infrared light at over 700 nm to 1100 nm.

15. The method of claim 12 comprising emittting circadian light.

16. The method of claim 12 comprising emittting combinations of light selected from the group consisting of far red light at 620 to 680 nm, infrared light at over 700 nm to 1100 nm and circadian light.

* * * * *